(12) United States Patent
Macinga et al.

(10) Patent No.: US 9,907,304 B2
(45) Date of Patent: Mar. 6, 2018

(54) ANTIMICROBIAL COMPOSITIONS

(75) Inventors: David R. Macinga, Stow, OH (US);
Sarah L. Edmonds, Canal Fulton, OH (US); Kristin E. Hartzell, Massillon, OH (US); Kelly A. Dobos, Cincinnati, OH (US); Carol A. Quezada, Canal Fulton, OH (US)

(73) Assignee: GOJO Industries, Inc., Akron, OH (US)

( * ) Notice: Subject to any disclaimer, the term of this patent is extended or adjusted under 35 U.S.C. 154(b) by 761 days.

(21) Appl. No.: 13/377,839

(22) PCT Filed: Jun. 14, 2010

(86) PCT No.: PCT/US2010/038453
§ 371 (c)(1),
(2), (4) Date: Feb. 9, 2012

(87) PCT Pub. No.: WO2010/147868
PCT Pub. Date: Dec. 23, 2010

(65) Prior Publication Data
US 2012/0129950 A1     May 24, 2012

Related U.S. Application Data

(60) Provisional application No. 61/187,041, filed on Jun. 15, 2009.

(51) Int. Cl.
| | | |
|---|---|---|
| *A01N 25/00* | (2006.01) | |
| *A01N 31/02* | (2006.01) | |
| *A61K 8/34* | (2006.01) | |
| *A61K 8/81* | (2006.01) | |
| *A61K 8/04* | (2006.01) | |
| *A61Q 19/00* | (2006.01) | |
| *A61Q 19/10* | (2006.01) | |
| *B05B 11/00* | (2006.01) | |

(52) U.S. Cl.
CPC .............. *A01N 31/02* (2013.01); *A61K 8/042* (2013.01); *A61K 8/34* (2013.01); *A61K 8/345* (2013.01); *A61K 8/8152* (2013.01); *A61Q 19/00* (2013.01); *A61Q 19/10* (2013.01); *B05B 11/30* (2013.01); *A61K 2800/48* (2013.01); *A61K 2800/5922* (2013.01); *A61K 2800/87* (2013.01)

(58) Field of Classification Search
CPC .......... A01N 31/02; A61K 8/042; A61K 8/34; A61K 8/345; A61K 8/8152; A61K 2800/48; A61K 2800/5922; A61K 2800/87; A61Q 19/00; A61Q 19/10; B05B 11/30
See application file for complete search history.

(56) References Cited

U.S. PATENT DOCUMENTS

| | | |
|---|---|---|
| 3,069,319 A | 12/1962 | Stearns |
| 3,954,960 A | 5/1976 | Valan |
| 4,692,277 A | 9/1987 | Siklosi |
| 4,933,177 A | 6/1990 | Grollier et al. |
| 4,956,170 A | 9/1990 | Lee |
| 4,961,921 A | 10/1990 | Chuang et al. |
| 5,167,950 A | 12/1992 | Lins |
| 5,266,598 A | 11/1993 | Ninomiya et al. |
| 5,340,570 A | 8/1994 | Wong et al. |
| 5,714,135 A | 2/1998 | Lee et al. |
| 5,968,204 A | 10/1999 | Wise |
| 5,985,294 A | 11/1999 | Peffly |
| 6,080,417 A | 6/2000 | Kramer et al. |
| 6,096,297 A | 8/2000 | Jones et al. |
| 6,096,349 A | 8/2000 | Petri et al. |
| 6,123,953 A | 9/2000 | Greff |
| 6,221,922 B1 * | 4/2001 | Policello et al. .............. 516/118 |
| 6,793,914 B2 | 9/2004 | Clarkson et al. |
| 6,846,352 B2 | 1/2005 | Yatake |
| 7,199,090 B2 | 4/2007 | Koivisto et al. |
| 7,247,295 B2 | 7/2007 | Schmaus et al. |
| 7,384,646 B2 | 6/2008 | Kobayashi et al. |
| 7,537,652 B2 | 5/2009 | Koganehira et al. |
| 7,566,460 B2 | 7/2009 | Asmus et al. |
| 7,582,681 B2 | 9/2009 | Schmaus et al. |
| 7,632,871 B2 | 12/2009 | Kobayashi et al. |
| 9,402,393 B2 | 8/2016 | Macinga et al. |
| 2004/0228820 A1 | 11/2004 | Elliott et al. |
| 2005/0222276 A1 | 10/2005 | Schmaus et al. |
| 2005/0228032 A1 | 10/2005 | Merianos et al. |
| 2007/0059331 A1 | 3/2007 | Schmaus et al. |

(Continued)

FOREIGN PATENT DOCUMENTS

| | | |
|---|---|---|
| EP | 0796610 A1 | 9/1997 |
| EP | 1764135 A1 | 3/2007 |

(Continued)

OTHER PUBLICATIONS

International Search Report for International Appl. No. PCT/US2010/038453 dated Feb. 23, 2011; 2 pages.

(Continued)

*Primary Examiner* — David Browe

(74) *Attorney, Agent, or Firm* — Calfee, Halter & Griswold LLP

(57) ABSTRACT

A method for rapid surface sanitization is provided, where the method includes contacting the surface with an effective amount of an antimicrobial composition comprising at least about 50 wt. % of a $C_{1-6}$ alcohol, based upon the total weight of the antimicrobial composition; and an efficacy-enhancing amount of a $C_{1-10}$ alkane diol.

12 Claims, No Drawings

(56) References Cited

U.S. PATENT DOCUMENTS

| | | |
|---|---|---|
| 2007/0065385 A1 | 3/2007 | Porter |
| 2007/0082039 A1 | 4/2007 | Jones, Jr. et al. |
| 2007/0138208 A1 | 6/2007 | Scholz et al. |
| 2007/0148101 A1 | 6/2007 | Synder et al. |
| 2007/0184013 A1* | 8/2007 | Snyder et al. ............... 424/78.3 |
| 2007/0185216 A1 | 8/2007 | Snyder et al. |
| 2007/0197704 A1 | 8/2007 | Walter et al. |
| 2007/0265352 A1* | 11/2007 | Roeding et al. ............. 514/738 |
| 2009/0004122 A1 | 1/2009 | Modak et al. |
| 2009/0018213 A1 | 1/2009 | Snyder |
| 2009/0082472 A1 | 3/2009 | Peters |
| 2009/0175806 A1 | 7/2009 | Modak et al. |
| 2009/0227675 A1 | 9/2009 | Lindstrom et al. |
| 2009/0238787 A1 | 9/2009 | Finke et al. |
| 2010/0068161 A1 | 3/2010 | Michael |
| 2010/0317743 A1 | 12/2010 | Macinga et al. |
| 2012/0129950 A1 | 5/2012 | Macinga et al. |

FOREIGN PATENT DOCUMENTS

| | | |
|---|---|---|
| EP | 1769824 A1 | 4/2007 |
| EP | 1967576 A1 | 9/2009 |
| JP | 11322591 A | 11/1999 |
| JP | 2004352688 A | 12/2004 |
| JP | 2005-526036 A | 9/2005 |
| JP | 2006273719 A | 10/2006 |
| JP | 2007145750 A | 6/2007 |
| JP | 2007-532542 A | 11/2007 |
| JP | 2009517152 A | 4/2009 |
| KR | 1020080108972 A | 12/2008 |
| WO | WO 9939687 A1 | 8/1999 |
| WO | WO9956715 A1 | 11/1999 |
| WO | WO 03003998 A1 | 1/2003 |
| WO | 2005030917 A1 | 4/2005 |
| WO | WO20051022276 A1 | 11/2005 |
| WO | WO2006033970 A2 | 3/2006 |
| WO | WO2007063065 A1 | 6/2007 |
| WO | 2007103687 A2 | 9/2007 |
| WO | WO2008067028 A2 | 6/2008 |
| WO | 2008132621 A1 | 11/2008 |
| WO | WO 2008/135085 * | 11/2008 ............. A61K 31/47 |
| WO | WO2008135085 A1 | 11/2008 |
| WO | 2009058802 A2 | 5/2009 |

OTHER PUBLICATIONS

International Preliminary Report on Patentability for International Appl. No. PCT/US2010/038453 dated Dec. 16, 2011; 8 pages.

International Search Report and Written Opinion of the International Searching Authority for technology related International Appl. No. PCT/US2008/081502 dated Dec. 16, 2010; 13 pages.

Notice of Reasons for Rejection for Japanese Patent Application No. 2012-516148, dated Jun. 23, 2014; and English Translation of said Rejection.

European Search Report for European Application No. EP10165683 dated Sep. 5, 2012; 6 pages.

* cited by examiner

ANTIMICROBIAL COMPOSITIONS

RELATED APPLICATIONS

This application is a national phase application of International Patent Application No. PCT/US2010/038453, filed on Jun. 14, 2010, and gains the benefit of U.S. Provisional No. 61/187,041, filed on Jun. 15, 2009, which are incorporated herein by reference.

TECHNICAL FIELD

One or more embodiments of the present invention provide a method for surface disinfection, where the method includes contacting the surface with an antimicrobial composition that includes an efficacy-enhancing amount of a $C_{1-10}$ alkane diol.

BACKGROUND OF THE INVENTION

There is a need in healthcare settings for efficacious broad-spectrum antimicrobial skin disinfection and hand wash products. Hand washing frequently is called the single most important measure to reduce the risks of transmitting micro organisms from one person to another or from one site to another on the same patient.

The United States Food and Drug Administration (FDA) developed performance standards for new and novel antiseptic compositions. These performance standards require a healthcare personnel hand wash to be broad spectrum and fast acting. The term broad spectrum is defined in this instance as having antimicrobial activity against a variety of gram positive and gram negative bacteria, and yeasts. The FDA set forth testing procedures by which new antiseptics are tested alongside previously approved products. Requirements for healthcare personnel hand wash are outlined in the FDA Tentative Final Monograph for Healthcare Antiseptic Drug Products (TFM) (Federal Register 59 [116], Jun. 17, 1994: pp. 31402-31452). The in vivo test procedure described beginning therein will hereinafter be referred to as the FDA TFM healthcare personnel hand wash test. Testing procedures have also been set forth in the TFM for surgical scrubs and pre-operative skin disinfecting products. A need continues to exist for healthcare personnel hand wash products with efficacy that meets the Monograph requirements, as well as other standards such as European norms.

Certain diols such as 1,2-alkane diols have been used in cosmetic products as humectants or moisturizers, and have even been shown to exhibit preservative ability when present in certain cosmetic formulations.

However, preservatives are not expected to show rapid efficacy such as that required for topical sanitizers and skin disinfecting compositions. Rather, preservatives exhibit their effects in 1 to 3 days or longer. That is, preservatives may be expected to inhibit microbial growth, but may not be sufficiently lethal to produce significant log kill of existing microbes. Additionally, many preservatives show poor activity against fungi. A need continues to exist for broad-spectrum antimicrobial products with rapid efficacy.

Others who have employed alkane diols as a preservative include U.S. Published Patent Application No. 2007/0059331, which teaches antimicrobial mixtures comprising one or more branched or unbranched alkane diols having 6-12 carbon atoms, and a tropolone. The mixtures are claimed to have a synergistic antimicrobial activity, and may be used as a preservative or antimicrobial active compound in a foodstuff or a cosmetic or a pharmaceutical formulation. Examples of formulations include sunscreen lotions and silicone emulsions.

U.S. Published Patent Application No. 2005/0222276 teaches synergistic mixtures of 1,2-alkane diols for the preservation of perishable products. They can also be used for the cosmetic treatment of microorganisms causing body odor, acne, mycoses, and for the treatment of microorganism on or in inanimate material.

U.S. Published Patent Application No. 2005/0228032 teaches a blend of 1,2-diol and phenoxyethanol and a co-biocide. The blend is suggested to control microbiological growth in personal care products.

However, a need remains for compositions having rapid, broad spectrum efficiency such as required for health care personal handwash.

SUMMARY OF THE INVENTION

In one or more embodiments, the present invention provides a method for skin sanitization, the method comprising contacting the skin with an effective amount of an antimicrobial composition comprising at least about 50 wt. % of a $C_{1-6}$ alcohol, based upon the total weight of the antimicrobial composition; and a $C_{6-10}$ alkane diol.

In one or more embodiments, the present invention provides a method for rapid surface sanitization, the method comprising contacting the surface with an effective amount of an antimicrobial composition comprising at least about 50 wt. % of a $C_{1-6}$ alcohol, based upon the total weight of the antimicrobial composition; and an efficacy-enhancing amount of a $C_{6-10}$ alkane diol.

In one or more embodiments, the present invention provides a foamable antimicrobial composition comprising at least about 50 wt. % of a $C_{1-6}$ alcohol, based upon the total weight of the antimicrobial composition; a $C_{6-10}$ alkane diol; and a foaming surfactant.

In one or more embodiments, the present invention provides an antimicrobial wipe composition comprising at least about 50 wt. % of a $C_{1-6}$ alcohol, based upon the total weight of the antimicrobial composition; and a $C_{6-10}$ alkane diol.

DETAILED DESCRIPTION OF ILLUSTRATIVE EMBODIMENTS

In one or more embodiments, the present method provides an antimicrobial composition. The physical form of the antimicrobial composition is not particularly limited, and in one or more embodiments, the composition may be presented as a liquid that is poured, pumped, sprayed, or otherwise dispensed, a gel, an aerosol, or a foam, including both aerosol and non-aerosol foams. In addition to being effective as a hand sanitizer, the antimicrobial composition of the present invention may be employed on a wide variety of surfaces or substrates, including skin, porous, and non-porous surfaces. In one or more embodiments, the antimicrobial composition may be presented as a wipe, i.e. a tissue or cloth that is wiped over a surface.

The antimicrobial composition comprises a $C_{1-6}$ alcohol and an enhancer. In one embodiment, the alcohol is a lower alkanol, i.e. an alcohol containing 1 to 6 carbon atoms. Typically, these alcohols have antimicrobial properties. Examples of lower alkanols include, but are not limited to, methanol, ethanol, propanol, butanol, pentanol, hexanol, and isomers and mixtures thereof. In one embodiment, the alcohol comprises ethanol, propanol, or butanol, or isomers or mixtures thereof. In another embodiment, the alcohol comprises ethanol.

Generally, the antimicrobial composition comprises at least about 30 percent by weight (wt. %) alcohol, based upon the total weight of the antimicrobial composition. In one embodiment, the antimicrobial composition comprises at least about 50 weight percent alcohol, in another embodiment, the antimicrobial composition comprises at least about 60 weight percent alcohol, in another embodiment, the antimicrobial composition comprises at least about 65 weight percent alcohol, in yet another embodiment, the antimicrobial composition comprises at least about 70 weight percent alcohol, and in still yet another embodiment, the antimicrobial composition comprises at least about 78 weight percent alcohol, based upon the total weight of antimicrobial composition. More or less alcohol may be required in certain instances, depending particularly on other ingredients and/or the amounts thereof employed in the composition. In certain embodiments, the antimicrobial composition comprises from about 50 weight percent to about 98 weight percent alcohol, in other embodiments, the antimicrobial composition comprises from about 60 weight percent to about 95 weight percent of alcohol, in yet other embodiments, the antimicrobial composition comprises from about 65 weight percent to about 90 weight percent of alcohol, and in still other embodiments, the antimicrobial composition comprises from about 70 weight percent to about 85 weight percent of alcohol, based upon the total weight of the antimicrobial composition.

Rapid antimicrobial efficacy is observed at lower concentrations of alcohol when an enhancer is present compared to when the enhancer is not present.

Advantageously, it has been found that antimicrobial compositions comprising alcohol and an efficacy-enhancing amount of an enhancer according to the present invention have increased efficacy against a broad spectrum of gram positive and gram negative bacteria, fungi, parasites, and viruses, when compared to antimicrobial compositions comprising alcohol without enhancer. In one or more embodiments, the diol comprises a straight chain diol. In one or more embodiments, the enhancer comprises one or more $C_{6-10}$ alkane diols, i.e. diols having a carbon chain length of 6 to 10. In one or more embodiments, the diol includes 1,2-hexanediol, 1,2-octanediol, 1,9-nonanediol, 1,2-decanediol, 1,10-decanediol, or a mixture thereof. 1,2-octanediol is sometimes referred to as caprylyl glycol. 1,2-decanediol is sometimes referred to as decylene glycol. In one or more embodiments, the diol comprises one or more $C_{6-8}$ alkane diols, i.e. diols having a carbon chain length of 6 to 8.

In one embodiment, an efficacy-enhancing amount of diol is at least about 0.02 wt. %, based upon the total weight of the antimicrobial composition, in another embodiment at least about 0.05, and in yet another embodiment at least about 0.1 wt. %, based upon the total weight of the antimicrobial composition.

Generally, an efficacy-enhancing amount of diol is from about 0.02 to about 10 wt. %, based upon the total weight of the antimicrobial composition. In one embodiment, the diol is present in an amount of from about 0.05 to about 5 weight percent, in another embodiment, the diol is present in an amount of from about 0.1 to about 1 wt. %, in yet another embodiment, from about 0.15 to about 0.8 wt. %, and in still yet another embodiment, from about 0.2 to about 0.75 wt. %, based upon the total weight of the antimicrobial composition. It will be understood that greater amounts of diol can be employed, if desired, and are expected to perform at least equally as well.

In certain embodiments, the diol is added to the antimicrobial composition as a solution or emulsion. In other words, the diol may be premixed with a carrier to form a diol solution or emulsion, with the proviso that the carrier does not deleteriously affect the sanitizing properties of the composition. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the diol is premixed to form a diol solution or emulsion, the amount of solution or emulsion that is added to the antimicrobial composition is selected so that the amount of diol falls within the ranges set forth hereinabove.

It is believed that, in one or more embodiments, the diol enhances antimicrobial efficacy by retarding evaporation of the alcohol and/or other antimicrobial agent if present, thereby providing increased contact time.

It is believed that, in one or more embodiments, the diol lowers the water activity of the alcoholic composition thus increasing the apparent alcohol concentration and thus increasing the antimicrobial activity of the alcoholic composition.

It is believed that, in one or more embodiments, the enhanced alcoholic composition maintains antimicrobial efficacy by killing or preventing the growth or establishment of transient microorganisms.

In one or more embodiments, the antimicrobial composition is a foamable alcoholic composition. Foamable antimicrobial alcoholic compositions in accordance with this invention include at least one alcohol, an $C_{1-10}$ alkane diol enhancer, and at least one foaming surfactant.

The foaming surfactant contributes foaming properties to the antimicrobial composition, and may include anionic, cationic, nonionic, zwitterionic, or amphoteric surfactants and their associated salts. Any foaming surfactant may be employed, with the proviso that they will not deleteriously affect the antimicrobial efficacy of the composition. Foaming surfactants suitable for alcoholic compositions are further described in co-pending U.S. patent application Ser. No. 11/438,664, which is hereby incorporated by reference in its entirety.

In one embodiment, the foaming surfactant includes a fluorosurfactant, a siloxane polymer surfactant, or a combination thereof. Fluorosurfactants include compounds that contain at least one fluorine atom. Examples of fluorosurfactants include perfluoroalkylethyl phosphates, perfluoroalkylethyl betaines, fluoroaliphatic amine oxides, fluoroaliphatic sodium sulfosuccinates, fluoroaliphatic stearate esters, fluoroaliphatic phosphate esters, fluoroaliphatic quaternaries, fluoroaliphatic polyoxyethylenes, and the like, and mixtures thereof.

In one embodiment, the fluorosurfactant contains a charged species, i.e. is anionic, cationic, or zwitterionic. Examples of fluorosurfactants containing a charged species include perfluoroalkylethyl phosphates, perfluoroalkylethyl betaines, fluoroaliphatic amine oxides, fluoroaliphatic sodium sulfosuccinates, fluoroaliphatic phosphate esters, and fluoroaliphatic quaternaries. Specific examples of fluorosurfactants include DEA-C8-18 perfluoroalkylethyl phosphate, TEA-C8-18 perfluoroalkylethyl phosphate, NH4-C8-18 perfluoroalkylethyl phosphate, and C8-18 perfluoroalkylethyl betaine.

In one embodiment, the fluorosurfactant includes a compound that may be represented by the formula $$[F_3CF_2C-(CF_2CF_2)_x-CH_2CH_2-O-P_2O_3]^-[R^1]^+$$

where $[R^1]^+$ includes DEA, TEA, $NH_4$, or betaine, and where x is an integer from about 4 to about 18.

Siloxane polymer surfactants may be generally characterized by containing one or more Si—O—Si linkages in the polymer backbone. The siloxane polymer surfactant may or may not include a fluorine atom. Therefore, some foaming surfactants may be classified as both fluorosurfactants and siloxane polymer surfactants. Siloxane polymer surfactants include organopolysiloxane dimethicone polyols, silicone carbinol fluids, silicone polyethers, alkylmethyl siloxanes, amodimethicones, trisiloxane ethoxylates, dimethiconols, quaternized silicone surfactants, polysilicones, silicone crosspolymers, and silicone waxes.

Examples of siloxane polymer surfactants include dimethicone PEG-7 undecylenate, PEG-10 dimethicone, PEG-8 dimethicone, PEG-12 dimethicone, perfluorononylethyl carboxydecal PEG 10, PEG-20/PPG-23 dimethicone, PEG-11 methyl ether dimethicone, bis-PEG/PPG-20/20 dimethicone, silicone quats, PEG-9 dimethicone, PPG-12 dimethicone, fluoro PEG-8 dimethicone, PEG 23/PPG 6 dimethicone, PEG 20/PPG 23 dimethicone, PEG 17 dimethicone, PEG5/PPG3 methicone, bis PEG20 dimethicone, PEG/PPG20/15 dimethicone copolyol and sulfosuccinate blends, PEG-8 dimethicone\dimmer acid blends, PEG-8 dimethicone\fatty acid blends, PEG-8 dimethicone\cold pressed vegetable oil\polyquaternium blends, random block polymers and mixtures thereof.

In one embodiment, the siloxane polymer surfactant includes a compound that may be represented by the formula $$R_2-Si(CH_3)_2-[O-Si(CH_3)_2]_a-[O-Si(CH_3)R_3]_b-O-Si(CH_3)_2-R_2$$

where $R_2$ and $R_3$ independently include a methyl group or a moiety that may be represented by the formula $$-(CH_2)_3-O-(CH_2CH_2O)_c-[CH_2CH(CH_3)O]_d-(CH_2CH_2O)_eH$$

with the proviso that both $R_2$ and $R_3$ are not $CH_3$, where a is an integer from about 3 to about 21, b is an integer from about 1 to about 7, c is an integer from about 0 to about 40, d is an integer from about 0 to about 40, and e is an integer from about 0 to about 40, with the proviso that $a \geq 3 \times b$ and that $c+d+e \geq 5$.

The amount of foaming surfactant is not particularly limited, so long as an effective amount to produce foaming is present. In certain embodiments, the effective amount to produce foaming may vary, depending upon the amount of alcohol and other ingredients that are present. In one or more embodiments, the alcoholic composition includes at least about 0.002 wt. % of foaming surfactant, based upon the total weight of the antimicrobial composition. In another embodiment, the antimicrobial composition includes at least about 0.01 wt. % of foaming surfactant, based upon the total weight of the antimicrobial composition. In yet another embodiment, the antimicrobial composition includes at least about 0.05 wt. % of foaming surfactant, based upon the total weight of the antimicrobial composition.

In one embodiment, the foaming surfactant is present in an amount of from about 0.002 to about 4 weight percent, based upon the total weight of the antimicrobial composition. In another embodiment, the foaming surfactant is present in an amount of from about 0.01 to about 2 weight percent, based upon the total weight of the antimicrobial composition. It is envisioned that higher amounts may also be effective to produce foam. All such weights as they pertain to listed ingredients are based on the active level, and therefore, do not include carriers or by-products that may be included in commercially available materials, unless otherwise specified.

In some embodiments, for economic or other reasons it may be desirable to limit the amount of fluorosurfactant used. Advantageously, stable foam can be produced from a composition according to the present invention containing greater than about 60 wt. % alcohol, and from about 0.002 to about 0.5 wt. % fluorosurfactant, based upon the total weight of the composition. In certain embodiments, the foamable composition includes greater than about 65 wt. % alcohol, and from about 0.002 to about 0.4 wt. % fluorosurfactant, based upon the total weight of the composition.

In other embodiments, it may be desirable to use higher amounts of foaming surfactant. For example, in certain embodiments where the foaming alcoholic composition of the present invention includes a cleansing or sanitizing product that is applied to a surface and then rinsed off, higher amounts of foaming surfactant may be employed. In these embodiments, the amount of foaming surfactant is present in amounts up to about 35 wt. %, based upon the total weight of the composition.

In one or more embodiments, the foaming surfactant is added directly to the antimicrobial composition. In other embodiments, the foaming surfactant is added to the antimicrobial composition as a solution or emulsion. In other words, the foaming surfactant may be premixed with a carrier to form a foaming surfactant solution or emulsion, with the proviso that the carrier does not deleteriously affect the foaming properties of the antimicrobial composition. Examples of carriers include any of the carriers described hereinabove for the diol enhancers. It will be understood that, when the foaming surfactant is premixed to form a foaming surfactant solution or emulsion, the amount of solution or emulsion that is added to the antimicrobial composition may be selected so that the amount of foaming surfactant falls within the ranges set forth hereinabove.

In certain embodiments, the alcoholic composition of the present invention further includes at least one foam booster. In one embodiment, the foam booster comprises a cationic oligomer or polymer, a collagen amino acid, an amaranth protein, or a soluble elastin. Foam boosters are further described in co-pending U.S. patent application Ser. No. 12/032,083, which is hereby incorporated by reference in its entirety.

The foamable composition of the present invention may be employed in any type of dispenser typically used for foam products. Advantageously, while the foamable composition can optionally be foamed by aerosolizing the composition, an aerosolized product is not necessary for foaming. Any dispenser that is capable of mixing the foamable alcoholic composition with air or an inert gas may be used. Inert gases include gas that does not substantially react or otherwise deleteriously affect the foamable composition. Examples of inert gases include nitrogen, argon, xenon, krypton, helium, neon, and radon. In one embodiment, the alcoholic composition is used in dispensers that employ foaming pumps, which combine ambient air or an inert gas and the alcoholic composition in a mixing chamber and pass the mixture through a mesh screen.

In one or more embodiments, the viscosity of the composition is less than about 100 mPas, in one embodiment less than about 50 mPas, and in another embodiment less than about 25 mPas.

In one or more embodiments, the antimicrobial composition may be formulated as a dispensable antimicrobial gel. In these embodiments, the antimicrobial composition may comprise a thickener, a neutralizer, and a plug-preventing additive, in addition to the alcohol and enhancer as described hereinabove.

In one or more embodiments, the antimicrobial may be thickened with polyacrylate thickeners such as those conventionally available and/or known in the art. Examples of polyacrylate thickeners include carbomers, acrylates/C 10-30 alkyl acrylate crosspolymers, copolymers of acrylic acid and alkyl (C5-C10) acrylate, copolymers of acrylic acid and maleic anhydride, and mixtures thereof.

In one or more embodiments, the polymeric thickener includes from about 0.5% to about 4% by weight of a cross-linking agent. Examples of cross-linking agents include the polyalkenyl polyethers.

Commercially available polymers of the polyacrylate type include those sold under the trade names Carbopol®, Acrysol® ICS-1, Polygel®, Sokalan®, Carbopol® 1623, Carbopol® 695, Ultrez 10, and Polygel® DB.

In one or more embodiments, the antimicrobial gel composition includes an effective amount of a polymeric thickener to adjust the viscosity of the antimicrobial gel to a viscosity range of from about 1000 to about 65,000 centipoise. In one embodiment, the viscosity of the antimicrobial gel is from about 5000 to about 35,000, and in another embodiment, the viscosity is from about 10,000 to about 25,000. The viscosity is measured by a Brookfield RV Viscometer using RV and/or LV Spindles at 22° C.+/−3° C.

As will be appreciated by one of skill in the art, the effective amount of thickener will vary depending upon a number of factors, including the amount of alcohol and other ingredients in the antimicrobial gel composition. In one or more embodiments, an effective amount of thickener is at least about 0.01 wt. %, based upon the total weight of the antimicrobial gel composition. In other embodiments, the effective amount is at least about 0.02 wt. %, in yet other embodiments at least about 0.05 wt. %, and it still other embodiments, at least about 0.1 wt. %. In one embodiment, the effective amount of thickener is at least about 0.5 wt. %, and in another embodiment, at least about 0.75 wt. %, based upon the total weight of the antimicrobial gel. In one or more embodiments, the compositions according to the present invention comprise up to about 10% by weight of the total composition of a polymeric thickener. In certain embodiments, the amount of thickener is from about 0.01 to about 1 wt. %, in another embodiment, from about 0.02 to about 0.4 wt. %, and in another embodiment, from about 0.05 to about 0.3 wt. %, based upon the total weight of the antimicrobial gel. In one embodiment, the amount of thickener is from about 0.1 to about 10 wt. %, in another embodiment from about 0.5% to about 5% by weight, in another embodiment from about 0.75% to about 2% wt. %, based upon the total weight of the antimicrobial gel.

In one or more embodiments, the antimicrobial gel may further comprise a neutralizer. The use of neutralizing agents to form salts of carbomer polymers is known. Examples of neutralizing agents include amines, alkanolamines, alkanolamides, inorganic bases, amino acids, including salts, esters and acyl derivatives thereof.

Examples of common neutralizers are shown in Table 1, along with the manufacturers of these neutralizers, and the suggested ratio (per one part polymeric thickener) to achieve neutralization (pH 7.0) when the polymeric thickener has an equivalent weight of about 76+/−4.

TABLE 1

| Trade Name | CTFA Name | Manufacturer | Neutralization Ratio Base/ Carbopol ® Polymer |
|---|---|---|---|
| NaOH (18%) | Sodium Hydroxide | | 2.3/1.0 |
| Ammonia (28%) | Ammonium Hydroxide | | 0.7/1.0 |
| KOH (18%) | Potassium Hydroxide | | 2.7/1.0 |
| L-Arginine | Arginine | Ajinomoto | 4.5/1.0 |
| AMP-95 ® | Aminomethyl Propanol | Angus | 0.9/1.0 |
| Neutrol ® TE | Tetrahydroxypropyl Ethylenediamine | BASF | 2.3/1.0 |
| TEA (99%) | Triethanolamine | | 1.5/1.0 |
| Tris Amino ® (40%)* | Tromethamine | Angus | 3.3/1.0 |
| Ethomeen ® C-25 | PEG-15 Cocamine | Akzo | 6.2/1.0 |
| Diisopropanolamine | Diisopropanolamine | Dow | 1.2/1.0 |
| Triisopropanolamine | Triisopropanolamine | Dow | 1.5/1.0 |

In one or more embodiments, the neutralizer may be selected based on the amount of alcohol that is to be gelled. Table 2 shows commonly recommended neutralizers for hydroalcoholic systems.

TABLE 2

| Up to % Alcohol | Neutralizer |
|---|---|
| 20% | Sodium Hydroxide |
| 30% | Potassium Hydroxide |
| 60% | Triethanolamine |
| 60% | Tris Amino |
| 80% | AMP-95 ® |
| 90% | Neutrol TE |
| 90% | Diisopropanolamine |
| 90% | Triisopropanolamine |
| >90% | Ethomeen C-25 |

In one or more embodiments, the antimicrobial composition further comprises one or more plug-preventing agents as co-additives. In one or more embodiments, the antimicrobial composition comprises a plug-preventing co-additive that includes an ester having from 2 to 6 ester groups or a polymeric ester that includes at least one ester group. In one embodiment, the plug-preventing additive comprises a monomeric or polymeric di-ester, tri-ester, tetra-ester, penta-ester, or hexa-ester, or a polymeric monoester. Ester plug-preventing additives are further described in co-pending International Patent Application No. PCT/US2008/081502, which is hereby incorporated by reference.

In one embodiment, the plug-preventing additive or co-additive is present in an amount of from about 0.005 to about 4 weight percent active, based upon the total weight of the antimicrobial gel composition. In another embodiment, the plug-preventing additive is present in an amount of from about 0.01 to about 1 weight percent, based upon the total weight of the antimicrobial gel composition, and in yet another embodiment, the plug-preventing additive is present in an amount of from about 0.02 to about 0.7 weight percent, based upon the total weight of the antimicrobial gel composition.

In one embodiment, the plug-preventing additive is added directly to the antimicrobial gel composition. In one or more other embodiments, the plug-preventing additive is added to the antimicrobial gel composition as a solution or emulsion. In other words, the plug-preventing additive may be premixed with a carrier to form a plug-preventing additive solution or emulsion, with the proviso that the carrier does not deleteriously affect the anti-clogging properties of the hydroalcoholic gel composition. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the plug-preventing additive is premixed to form a plug-preventing additive solution or emulsion, the amount of solution or emulsion that is added to the antimicrobial gel composition is selected so that the amount of plug-preventing additive falls within the ranges set forth hereinabove.

In one or more embodiments, the balance of the antimicrobial gel composition includes water or other suitable solvent. In one embodiment, one or more volatile silicone-based materials are included in the formulation to further aid the evaporation process. Exemplary volatile silicones have a lower heat of evaporation than alcohol. In certain embodiments, use of silicone-based materials can lower the surface tension of the fluid composition. This provides greater contact with the surface. In one embodiment, the silicone-based material, such as cyclomethicone, trimethylsiloxy silicate or a combination thereof, may be included in the formulation at a concentration of from about 4 wt. % to about 50 wt. % and in another embodiment from about 5 wt. % to about 35 wt. %, and in yet another embodiment from about 11 wt. % to about 25 wt. %, based upon the total weight of the antimicrobial gel composition.

The dispensable antimicrobial gel composition may be prepared by simply mixing the components together. The order of addition is not particularly limited. In one embodiment, the antimicrobial gel composition is prepared by a method comprising dispersing the polymeric thickener in alcohol with slow to moderate agitation, adding water, and then adding a plug-preventing additive, and mixing until the mixture is homogeneous. In other embodiments, the antimicrobial gel composition is prepared by a method comprising dispersing the polymeric thickener in water with slow to moderate agitation, adding alcohol, a plug-preventing additive, and mixing until the mixture is homogeneous. In one or more embodiments, a neutralizer is added to the mixture to neutralize the thickener and form the gel. Those of skill in the art will understand that optional ingredients may be added at various points during the mixing process. It will also be understood that a gel may be formed without a neutralizer if the thickener is one that swells when mixed with water or alcohol.

The antimicrobial gel composition of the present invention may be employed in any type of dispenser typically used for gel products, for example pump dispensers. A wide variety of pump dispensers are suitable. Pump dispensers may be affixed to bottles or other free-standing containers. Pump dispensers may be incorporated into wall-mounted dispensers. Pump dispensers may be activated manually by hand or foot pump, or may be automatically activated. Useful dispensers include those available from GOJO Industries under the designations NXT® and TFX™ as well as traditional bag-in-box dispensers. Examples of dispensers are described in U.S. Pat. Nos. 5,265,772, 5,944,227, 6,877,642, 7,028,861, and U.S. Published Application Nos. 2006/0243740 A1 and 2006/0124662 A1, all of which are incorporated herein by reference. In one or more embodiments, the dispenser includes an outlet such as a nozzle, through which the antimicrobial gel composition is dispensed.

In one or more embodiments, the antimicrobial composition is a wipe composition. Wipe antimicrobial alcoholic compositions in accordance with this invention include at least one alcohol, a $C_{1-10}$ alkane diol enhancer, and are applied to a wipe substrate.

Wipe substrates used in antimicrobial wipes are further described in U.S. Pat. Nos. 5,686,088, 6,410,499, 6,436,892, 6,495,508, 6,844,308. In one or more embodiments, the wipe may comprise a laminate formed by spunbonding/meltblowing/spunbonding (SMS). Generally, an SMS material contains a meltblown web sandwiched between two exteriors spunbond webs. SMS materials are further described in U.S. Pat. Nos. 4,041,203, 5,169,706, 5,464,688, and 4,766,029, and are commercially available, for example from Kimberly-Clark Corporation under marks such as Spunguard 7 and Evolution 7. The SMS laminate may be treated or untreated.

As described hereinabove, the antimicrobial composition of this invention includes an alcohol and an enhancer. The composition can further comprise a wide range of optional ingredients, with the proviso that they do not deleteriously affect the sanitizing efficacy of the composition. By deleterious is meant that the decrease in the log reduction according to the FDA TFM healthcare personnel hand wash test is not de minimus, or in other words, the log reduction does not decrease by more than about 0.5. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, humectants, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

In certain embodiments, the antimicrobial composition comprises one or more humectants. Examples of humectants include propylene glycol, dipropyleneglycol, hexylene glycol, 1,4-dihydroxyhexane, 1,2,6-hexanetriol, sorbitol, butylene glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, lactic acid, sodium pyrrolidone carboxylic acid, hyaluronic acid, chitin, and the like. In one embodiment, the humectant is present in an amount of from about 0.1 to about 20% by weight, based upon the total weight of the antimicrobial composition. In another embodiment the humectant is present in an amount of from about 1 to about 8% by weight, in another embodiment from about 2 to about 3% by weight, based upon the total weight of the antimicrobial composition.

In these or other embodiments, the antimicrobial composition comprises one or more conditioning or moisturizing esters. Examples of esters include cetyl myristate, cetyl myristoleate, and other cetyl esters, diisopropyl sebacate, and isopropyl myristate. In one embodiment, the ester is present in an amount of up to 10% by weight, based upon the total weight of the antimicrobial composition. In another embodiment the ester is present in an amount of from about 0.5 to about 5% by weight, in another embodiment from about 1 to about 2% by weight, based upon the total weight of the antimicrobial composition.

In one or more embodiments, the antimicrobial composition includes one or more emulsifying agents. Examples of emulsifying agents include stearyl alcohol, sorbitan oleate trideceth-2, poloxamers, and PEG/PPG-20/6 dimethicone. In one embodiment, the emulsifying agent is present in an amount of up to about 10% by weight, based upon the total weight of the antimicrobial composition. In another embodiment the emulsifying agent is present in an amount of from about 0.1 to about 5% by weight, in another embodiment from about 0.5 to about 2% by weight, based upon the total weight of the antimicrobial composition.

In one embodiment, the antimicrobial composition includes one or more thickeners and optionally one or more stabilizers. Examples of thickeners and stabilizers include hydroxyethyl cellulose hydroxypropyl cellulose, methyl cellulose, carboxymethyl cellulose, and ammonium acryloyldimethyltaurate/VP copolymer. In one embodiment, where the thickener or stabilizer is starch-based, the thickener or stabilizer is present in an amount of up to about 10% by weight, in another embodiment in an amount of from about 0.1 to about 5% by weight, in yet another embodiment from about 0.2 to about 1% by weight, based upon the total weight of the antimicrobial composition. In other embodiments, where the thickener or stabilizer is a synthetic polymer, the thickener or stabilizer is present in an amount of up to about 15% by weight, in another embodiment in an amount of from about 0.1 to about 10% by weight, in yet another embodiment from about 1 to about 2% by weight, based upon the total weight of the antimicrobial composition.

In one or more embodiments, the antimicrobial composition includes one or more solubilizers. Examples of solubilizers include PEG-40 hydrogenated castor oil, polysorbate-80, PEG-80 sorbitan laurate, ceteareth-20, oleth-20, PEG-4, and propylene glycol. The amount of solubilizer is not particularly limited, so long as it does not deleteriously affect the sanitizing efficacy of the composition.

In one or more embodiments, the antimicrobial composition includes one or more antiviral agents or antiviral enhancers. Examples of antiviral agents include botanicals such as rosmarinic acid, tetrahydrocurcuminoids, oleuropen, oleanolic acid, aspalathus linearis extract, white tea, red tea, green tea extract, neem oil limonoids, coleus oil, licorice extract, burnet, ginger & cinnamon extracts, alpha-glucan oligosaccharide, perilla ocymoides leaf powder, camphor, camellia oleifera leaf extract, ginger, menthol, eucalyptus, capillisil hc, hydroxyprolisilane cn, sandlewood oil/resin, calendula oil, rosemary oil, lime/orange oils, and hop acids. When used, the antiviral agents are present in amounts of from about 0.1 to about 1 percent by weight, based upon the total weight of the antimicrobial composition.

Examples of antiviral enhancers include proton donors, cationic oligomers and polymers, chaotropic agents, and copper and zinc compounds. Antiviral enhancers are further described in co-pending U.S. Patent Application Publications 2007/0184013, 2007/0185216, and 2009/0018213, all of which are hereby incorporated by reference.

It has been discovered that the combination of alcohol and enhancer exhibits enhanced antimicrobial efficacy. Advantageously, auxiliary antimicrobials, some of which can be harsh on skin, are not required. In certain embodiments, the antimicrobial composition does not contain any auxiliary antimicrobial ingredients. Any antimicrobial ingredient other than the combination of alcohol and enhancer may be referred to as an auxiliary antimicrobial agent. In one embodiment, the amount of auxiliary antimicrobial agent (including preservatives) is less than about 0.1 wt. %, in another embodiment, less than about 0.05 wt. %, based upon the total weight of the antimicrobial composition. In another embodiment, the antimicrobial composition is devoid of auxiliary antimicrobial agents.

It is envisioned that, in other embodiments, auxiliary antimicrobial agents could be included, with the proviso that the antimicrobial ingredient does not deleteriously affect the sanitizing properties of the composition. Examples of auxiliary antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecanediimidi amide; 2-bromo-2-nitropropane-1; 3-diol, benzalkonium chloride; cetylpyridinium chloride; alkylbenzyldimethylammonium chlorides; iodine; phenol, bisphenol, diphenyl ether, phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; benzethonium chloride; methylbenzethonium chloride; glyceryl laurate, transition metal compounds such as silver, copper, magnesium, zinc compounds, hydrogen peroxide, chlorine dioxide, anilides, bisguanidines, tropolone, and mixtures thereof. When used, the auxiliary antimicrobial agents are present in amounts of from about 0.1 to about 1 wt. %, based upon the total weight of the antimicrobial composition.

Advantageously, certain ingredients that have been designated as critical to current antiseptic compositions can be limited in the antimicrobial composition of the present invention. For example, zinc compounds such as organic salts of zinc, zinc gluconate, zinc pyrithione, or zinc omadine are not necessary, and can be limited, if desired, to less than about 0.5 wt. %, or in another embodiment to less than about 0.1 wt. %, based upon the total weight of the antimicrobial composition. In another embodiment, the antimicrobial composition is devoid of organic salts of zinc.

In one or more embodiments, the amount of acid may be limited. More specifically, in one or more embodiments, the amount of organic acid may be limited. In one or more embodiments, the amount of any of the following acids may be limited: citric acid, glycolic acid, lactic acid, malic acid, tartaric acid, and acetic acid. When limited, in one or more embodiments, the amount of acid may be less than 0.125 wt. %, in other embodiments less than about 0.08 wt. %, based upon the total weight of the antimicrobial composition. In another embodiment, the antimicrobial composition is devoid of citric acid, glycolic acid, lactic acid, malic acid, tartaric acid, and acetic acid.

In one or more embodiments, the amount of essential oil is less than 0.1 wt. %, or in another embodiment less than about 0.05 wt. %, based upon the total weight of the antimicrobial composition. In another embodiment, the antimicrobial composition is devoid of essential oils. More specifically, in one embodiment, the antimicrobial composition contains less than 0.1 wt. %, in another embodiment less than 0.05, and in another embodiment, is devoid of any of the following essential oils: cinnamon oil, basil oil, bergamot oil, clary sage oil, ylang-ylang oil, neroli oil, sandalwood oil, frankincense oil, ginger oil, peppermint oil, lavender oil, jasmine absolute, geranium oil bourbon, spearmint oil, clove oil, patchouli oil, rosemary oil, rosewood oil, sandalwood oil, tea tree oil, vanilla oil, lemongrass oil, cedarwood oil, balsam oils, tangerine oil, Hinoki oil, Hiba oil, ginko oil, eucalyptus oil, lemon oil, orange oil, sweet orange oil, and calendula oil, wherein the above amounts are based upon the total weight of the antimicrobial composition.

In one or more embodiments, the amount of specific constituents of essential oils is also limited. More specifically, in one embodiment, the antimicrobial composition contains less than 0.1 wt. %, in another embodiment less than 0.05, and in another embodiment, is devoid of any of the following constituents of essential oils: farnesol, nerolidol, bisabolol, apritone, chamazulene, santalol, zingiberol, carotol, and caryophyllen, curcumin, 1-citronellol, α-amyl-cinnarnaldehyde, lyral, geraniol, farnesol, hydroxycitronellal, isoeugenol, eugenol, camphor, eucalyptol, linalool, citral, thymol, limonene and menthol, wherein the above amounts are based upon the total weight of the antimicrobial composition.

Advantageously, traditional preservative agents are not required. In one or more embodiments, the amount of traditional preservative agents such as potassium sorbate, parabens, and iodopropynyl butylcarbomate (IPBC) is limited. In one or more embodiments, the antimicrobial composition contains less than about 0.1 wt. %, in another embodiment less than about 0.05 wt. %, or in another embodiment less than about 0.01 wt. % of traditional preservative agents, based upon the total weight of the antimicrobial composition. In another embodiment, the antimicrobial composition is devoid of traditional preservative agents.

Indeed, any component other than the alcohol and diol enhancer is not necessary to achieve antimicrobial efficacy and can optionally be limited to less than about 0.5 wt. %, if desired to less than about 0.1 wt. %, if desired to less than about 0.01 wt. %, or if desired to less than about 0.001 wt. %. It will be understood that the balance of the antimicrobial composition may, in certain embodiments, include water or other suitable solvent. In one embodiment, the antimicrobial composition is devoid of any component other than alcohol, diol enhancer and optionally water or other suitable solvent.

The antimicrobial composition may be prepared by simply mixing the components together. In one embodiment, where one or more components is obtained as a solid powder, the antimicrobial composition is prepared by a method comprising dispersing the solid powder in water to form a gel, adding alcohol with slow to moderate agitation, and then adding other ingredients as desired, and mixing until the mixture is homogeneous.

As stated hereinabove, the antimicrobial composition of the present invention may be embodied in a variety of forms, including as a liquid, gel, foam or wipe composition. Surprisingly, it has been found that the viscosity of the liquid antimicrobial composition does not affect the sanitizing efficacy of the composition. For example, in one or more embodiments of the present invention, the same amount of log reduction is achieved with a liquid antimicrobial composition having a viscosity of 5 centipoise (cPs) and an antimicrobial composition having a viscosity of about 2000 cPs. Thus it will be understood that the viscosity of the antimicrobial composition of the present invention is not limited.

In one embodiment, where the antimicrobial composition is in liquid form, the percent solids of the antimicrobial composition is less than about 6 percent, in another embodiment, less than about 5 percent, in yet another embodiment, less than about 4 percent, in still another embodiment, less than about 3 percent, in another embodiment, less than about 2 percent, in yet another embodiment, less than about 1 percent. The percent solids can be determined by various methods known in the art.

In one or more embodiments, the pH of the antimicrobial composition is from about 1.5 to about 10, in another embodiment from about 4.5 to about 9.5, in another embodiment from about 7 to about 8.

Unexpectedly, when an enhancer is combined with alcohol according to the present invention, rapid antimicrobial activity is enhanced, i.e. potentiated. In one or more embodiments, the antimicrobial composition is effective in killing gram negative and gram positive bacteria, fungi, parasites, non-enveloped and enveloped viruses. In one or more embodiments, the antimicrobial composition has rapid antimicrobial efficacy against bacteria such as *Staphylococcus aureus*, methicillin-resistant *S. aureus, Escherichia coli, Pseudomonas aeruginosa, Serratia marcescens*, and fungi such as *Candida albicans* and *Aspergillus niger*. In one or more embodiments, the antimicrobial composition has rapid efficacy against skin microflora, including resident and transient skin microflora.

Thus, the present invention further provides a method for killing or inactivating microbes on a surface comprising applying, to the surface, an effective amount of an antimicrobial composition as described herein. The antimicrobial composition may be employed on a wide variety of surfaces or substrates, including skin, porous, and non-porous surfaces.

In one or more embodiments, the antimicrobial composition of the present invention is applied topically to mammalian skin. In these embodiments, the composition is not applied to the eyes, ears, nose, mouth, or any membranes thereof. In one embodiment, the methods of bringing the antimicrobial composition into contact with a microbe on human skin includes applying an amount of the composition to the skin, and allowing the composition to remain in contact with the skin for a suitable amount of time. In other embodiments, the composition may be spread over the surface of the skin, rubbed in, rinsed off, allowed to dry via evaporation, or wiped off.

Thus, the present invention provides a method for skin sanitization, the method comprising contacting mammalian skin with an effective amount of an antimicrobial composition comprising at least 30 wt. % alcohol, based upon the total weight of the antimicrobial composition, and an efficacy-enhancing amount of at least one $C_{6-10}$ alkane diol. In one or more embodiments, the present invention provides a method for hand sanitization.

Advantageously, the antimicrobial composition of the present invention may be used as a healthcare personnel hand wash. In one or more embodiments, the present invention provides an antimicrobial composition that meets the standards of the FDA Tentative Final Monograph for Healthcare Antiseptic Drug Products (TFM) (Federal Register 59 [116], Jun. 17, 1994: pp. 31402-31452) for healthcare personnel hand wash.

In the FDA TFM test for healthcare personnel hand wash and other standard tests, test procedures include multiple wash cycles. In each cycle, a subject surface is contaminated with a test organism and the surface is washed with a test product. After a specified number of wash cycles, the surface is rinsed and the rinsing liquid is tested to determine what log reduction has been achieved by the test product. For example, in the FDA TFM test for healthcare personnel hand wash, the following protocol is followed for leave on products such as alcoholic compositions. The hands of a test subject are contaminated with a test organism such as *Serratia marcescens*, and washed using the test product. The hands are then placed into sterile gloves, a bacterial recovery solution is added and hands are massaged by a technician for a preset amount of time to recover viable bacteria from the hands. The recovery solution is plated to determine the log reduction achieved by one wash. The hands of the test subject are again contaminated with the test organism and washed using the test product. For a third time the hands of the test subject are again contaminated with the test organism and washed using the test product. After the third wash the hands are again placed into gloves and viable bacteria are recovered to determine the log reduction after the third wash. The cycle of contamination and wash is repeated until, after the seventh wash, the hands are again placed into gloves and viable bacteria are recovered to determine the log reduction after the seventh wash. The cycle of contamination and wash is repeated until, after the tenth wash, the hands are again placed into gloves and viable bacteria are recovered to determine the log reduction after the tenth wash. According to the FDA TFM test, healthcare personnel hand wash formulations must reduce the number of bacteria on the hands by 2 $log_{10}$ after one wash and reduce the number of bacteria on the hands by 3 $log_{10}$ after ten washes. It should be noted that the FDA TFM test refers to "wash" for both rinse-off and leave-on products, and therefore the instant specification may do the same.

Many alcoholic products achieve a minimum 3 log reduction after one wash using the FDA TFM test. However, many alcoholic products fail to achieve a minimum of 3 log reduction after the tenth wash using the FDA TFM test. In fact, a number of alcoholic products exhibit a reduction in log reduction over successive washes.

Advantageously, the enhanced alcoholic compositions of the present invention do not exhibit a reduction in efficacy over successive washes, when tested according to the FDA TFM healthcare personnel hand wash or similar protocol.

In one or more embodiments, the antimicrobial composition of the present invention meets or exceeds the requirement of 2 $log_{10}$ reduction after a first wash, and 3 $log_{10}$ reduction after a tenth wash. In one or more embodiments, enhanced alcoholic compositions according to the present invention provide a log reduction of at least about 3 after one wash, and at least about 3 after ten washes. In certain embodiments, the antimicrobial composition demonstrates a cumulative effect and surpasses the requirements of the FDA TFM healthcare personnel hand wash test by achieving 3 $log_{10}$ reduction after wash 1 and 4 $log_{10}$ reduction after wash 10.

In one or more embodiments, the $log_{10}$ reduction of a test organism achieved by a third wash utilizing the enhanced composition of the present invention is at least equal to the $log_{10}$ reduction achieved by a first wash cycle. In one or more embodiments, the $log_{10}$ reduction of a test organism achieved by a tenth wash utilizing the enhanced composition of the present invention is at least equal to the $log_{10}$ reduction achieved by a first wash cycle.

When evaluated according to tests that require multiple wash cycle protocols, enhanced alcoholic compositions according to the present invention provide a log reduction that is maintained or even improved over multiple wash cycles. Furthermore, the enhanced composition unexpectedly provides cumulative activity, i.e. the efficacy of the enhanced composition increases with multiple uses.

The sustained efficacy exhibited by the enhanced alcoholic antimicrobial compositions of the present invention make them useful as surgical scrub compositions. Requirements for in vitro and in vivo testing of surgical hand scrubs are outlined in the FDA Tentative Final Monograph for Healthcare Antiseptic Drug Products (TFM) (Federal Register 59 [116], Jun. 17, 1994: pp. 31445-31448). The in vivo test procedure described beginning on page 31445 will hereinafter be referred to as the FDA TFM surgical hand scrub test. The antimicrobial efficacy of Surgical Scrubs can also be tested by any appropriate recognized test to demonstrate adequate disinfection of resident skin flora. Examples of such tests are ASTM E 1115-02, "Standard Test Method for Evaluation of Surgical Hand Scrub Formulations" (ASTM International) and EN 12791:2005, "Chemical disinfectants and antiseptics, Surgical hand disinfection, Test method and requirement (phase 2, step 2)," (CEN-Comitée Européen de Normalisation, Brussels, Belgium).

The antimicrobial composition and method of the present invention provides rapid antimicrobial efficacy upon a single use, without requiring auxiliary antimicrobial agents. The rapid, broad-spectrum efficacy makes the compositions useful as skin preparations as described and tested in ASTM E 1173-01 provides "Standard Test Method for Evaluation of Preoperative, Precatheterization, or Preinjection Skin Preparations" and FDA Tentative Final Monograph for Healthcare Antiseptic Drug Products (TFM) (Federal Register 59 [116], Jun. 17, 1994: pp. 31402-31452).

In one or more embodiments, the present invention provides an antimicrobial composition that meets the standards of one or more of EN1040 for basic bactericidal activity, EN1275 for basic fungicidal activity, EN1500 for activity of products for use as a hygienic hand rub, EN14348 for tuberculoidal activity, EN14476 for virucidal activity, and EN12791 for surgical hand disinfection.

More generally, in one or more embodiments, the method provides a log reduction of transient skin microflora of at least about 1 in less than about 1 minute. In other embodiments, the method provides a log reduction of transient skin microflora of at least about 2 in less than about 1 minute. In yet other embodiments, the method provides a log reduction of transient skin microflora of at least about 3 in less than about 1 minute. In other embodiments, the method provides a log reduction of transient skin microflora of at least about 4 in less than about 1 minute. In yet other embodiments, the method provides a log reduction of transient skin microflora of at least about 5 in less than about 1 minute.

In one or more embodiments, the method provides a log reduction against transient skin microflora of at least about 1 in less than about 30 seconds. In other embodiments, the method provides a log reduction against transient skin microflora of at least about 2 in less than about 30 seconds. In yet other embodiments, the method provides a log reduction against transient skin microflora of at least about 3 in less than about 30 seconds. In other embodiments, the method provides a log reduction against transient skin microflora of at least about 4 in less than about 30 seconds. In yet other embodiments, the method provides a log reduction against transient skin microflora of at least about 5 in less than about 30 seconds.

In one or more embodiments, the method provides a log reduction against transient skin microflora of at least about 1 in less than about 15 seconds. In other embodiments, the method provides a log reduction against transient skin microflora of at least about 2 in less than about 15 seconds. In yet other embodiments, the method provides a log reduction against transient skin microflora of at least about 3 in less than about 15 seconds. In other embodiments, the method provides a log reduction against transient skin microflora of at least about 4 in less than about 15 seconds. In yet other embodiments, the method provides a log reduction against transient skin microflora of at least about 5 in less than about 15 seconds.

In one or more embodiments, the method provides a log reduction against *Escherichia coli* of at least about 1 in less than about 1 minute. In other embodiments, the method provides a log reduction against *Escherichia coli* of at least about 2 in less than about 1 minute. In yet other embodiments, the method provides a log reduction against the mixture of at least about 3 in less than about 1 minute. In other embodiments, the method provides a log reduction against *Escherichia coli* of at least about 4 in less than about 1 minute. In yet other embodiments, the method provides a log reduction against *Escherichia coli* of at least about 5 in less than about 1 minute.

In one or more embodiments, the method provides a log reduction against *Escherichia coli* of at least about 1 in less than about 30 seconds. In other embodiments, the method provides a log reduction against *Escherichia coli* of at least about 2 in less than about 30 seconds. In yet other embodiments, the method provides a log reduction against *Escherichia coli* of at least about 3 in less than about 30 seconds. In other embodiments, the method provides a log reduction against *Escherichia coli* of at least about 4 in less than about 30 seconds. In yet other embodiments, the method provides a log reduction against *Escherichia coli* of at least about 5 in less than about 30 seconds.

In one or more embodiments, the method provides a log reduction against *Escherichia coli* of at least about 1 in less than about 15 seconds. In other embodiments, the method provides a log reduction against *Escherichia coli* of at least about 2 in less than about 15 seconds. In yet other embodiments, the method provides a log reduction against *Escherichia coli* of at least about 3 in less than about 15 seconds. In other embodiments, the method provides a log reduction against *Escherichia coli* of at least about 4 in less than about 15 seconds. In yet other embodiments, the method provides a log reduction against *Escherichia coli* of at least about 5 in less than about 15 seconds.

In one or more embodiments, the method provides a log reduction against *Serratia marcescens* of at least about 1 in less than about 1 minute. In other embodiments, the method provides a log reduction against *Serratia marcescens* of at least about 2 in less than about 1 minute. In yet other embodiments, the method provides a log reduction against the mixture of at least about 3 in less than about 1 minute. In other embodiments, the method provides a log reduction against *Serratia marcescens* of at least about 4 in less than about 1 minute. In yet other embodiments, the method provides a log reduction against *Serratia marcescens* of at least about 5 in less than about 1 minute.

In one or more embodiments, the method provides a log reduction against *Serratia marcescens* of at least about 1 in less than about 30 seconds. In other embodiments, the method provides a log reduction against *Serratia marcescens* of at least about 2 in less than about 30 seconds. In yet other embodiments, the method provides a log reduction against *Serratia marcescens* of at least about 3 in less than about 30 seconds. In other embodiments, the method provides a log reduction against *Serratia marcescens* of at least about 4 in less than about 30 seconds. In yet other embodiments, the method provides a log reduction against *Serratia marcescens* of at least about 5 in less than about 30 seconds.

In one or more embodiments, the method provides a log reduction against *Serratia marcescens* of at least about 1 in less than about 15 seconds. In other embodiments, the method provides a log reduction against *Serratia marcescens* of at least about 2 in less than about 15 seconds. In yet other embodiments, the method provides a log reduction against *Serratia marcescens* of at least about 3 in less than about 15 seconds. In other embodiments, the method provides a log reduction against *Serratia marcescens* of at least about 4 in less than about 15 seconds. In yet other embodiments, the method provides a log reduction against *Serratia marcescens* of at least about 5 in less than about 15 seconds.

More generally, in one or more embodiments, the method provides a log reduction of resident skin microflora of at least about 1 in less than about 1 minute. In other embodiments, the method provides a log reduction of resident skin microflora of at least about 2 in less than about 1 minute. In yet other embodiments, the method provides a log reduction of resident skin microflora of at least about 3 in less than about 1 minute. In other embodiments, the method provides a log reduction of resident skin microflora of at least about 4 in less than about 1 minute. In yet other embodiments, the method provides a log reduction of resident skin microflora of at least about 5 in less than about 1 minute.

In one or more embodiments, the method provides a log reduction against resident skin microflora of at least about 1 in less than about 30 seconds. In other embodiments, the method provides a log reduction against resident skin microflora of at least about 2 in less than about 30 seconds. In yet other embodiments, the method provides a log reduction against resident skin microflora of at least about 3 in less than about 30 seconds. In other embodiments, the method provides a log reduction against resident skin microflora of at least about 4 in less than about 30 seconds. In yet other embodiments, the method provides a log reduction against resident skin microflora of at least about 5 in less than about 30 seconds.

In one or more embodiments, the method provides a log reduction against resident skin microflora of at least about 1 in less than about 15 seconds. In other embodiments, the method provides a log reduction against resident skin microflora of at least about 2 in less than about 15 seconds. In yet other embodiments, the method provides a log reduction against resident skin microflora of at least about 3 in less than about 15 seconds. In other embodiments, the method provides a log reduction against resident skin microflora of at least about 4 in less than about 15 seconds. In yet other embodiments, the method provides a log reduction against resident skin microflora of at least about 5 in less than about 15 seconds.

Any amount of the antimicrobial composition may be used for each application, so long as it is at least an effective amount to contact substantially the entire target surface and keep it wet for at least 15 to 30 seconds. In one embodiment, an effective amount is at least about 1.5 milliliters (mL), in another embodiment at least about 2 mL, in yet another embodiment, at least about 2.5 mL, in yet another embodiment, at least about 3.0 mL, in yet another embodiment, at least about 4.5 mL, and in yet another embodiment, at least about 5 mL. Advantageously, the effective amount of antimicrobial composition according to the present invention, i.e. the minimum amount necessary to contact substantially the entire target surface, is also an amount that is effective to achieve adequate efficacy. Other products may not achieve adequate efficacy if only an effective amount to contact substantially the entire target surface is used. It will be understood that it is advantageous to achieve adequate efficacy while using a small amount of product. This is true for economic reasons, as well as because the amount of time required for the product to be rubbed into the skin and or evaporated/dried is reduced when less product is used.

Advantageously, in one or more embodiments, the present invention further provides compositions and methods with rapid antimicrobial efficacy against gram positive and gram negative bacteria and fungi, as well as broad spectrum virucidal efficacy against one or more enveloped or one or more non-enveloped viruses. Examples of enveloped viruses include Herpes virus, Influenza virus; Paramyxovirus, Respiratory syncytial virus, Corona virus, HIV, Hepatitis B virus, Hepatitis C virus, SARS-CoV, and Toga virus. Non-enveloped viruses, sometimes referred to as "naked" viruses, include the families Picornaviridae, Reoviridae, Caliciviridae, Adenoviridae and Parvoviridae. Members of these families include Rhinovirus, Poliovirus, Adenovirus, Hepatitis A virus, Norovirus, Papillomavirus, and Rotavirus.

In one or more embodiments, the method comprises contacting enveloped or non-enveloped virus particles with an enhanced alcoholic composition comprising a $C_{1-6}$ alcohol, a $C_{6-10}$ alkane diol, and an efficacy-enhancing amount of one or more antiviral enhancers selected from the group consisting of cationic oligomers and polymers, proton donors, chaotropic agents, and mixtures thereof. Antiviral enhancers are further described in co-pending published patent application nos. U.S. 2007/0185216 and 2007/0184013, both of which are hereby incorporated by reference.

In order to demonstrate the practice of the present invention, the following examples have been prepared and tested. The examples should not, however, be viewed as limiting the scope of the invention. The claims will serve to define the invention.

EXAMPLES

Examples 1-3 were foamable formulations that were dispensed as foams. Example 1 contained 70 wt. % ethanol, and conventional amounts of PEG-10 dimethicone, PEG-12 dimethicone, glycerin, fragrance, propylene glycol, isopropyl myristate, and tocopheryl acetate. The composition of Example 2 was identical to Example 1 except that Example 2 also included 0.5 wt. % 1,2-octanediol. Example 3 contained 62 wt. % ethanol, 0.5 wt. % 1,2-octanediol, and conventional amounts of PEG-10 dimethicone, PEG-12 dimethicone, glycerin, fragrance, propylene glycol, isopropyl myristate, and tocopheryl acetate. Example 4 was a commercially available liquid formulation that contained about 63% by volume isopropanol, and is marketed by Steris Corporation under the trademark CalStat®. Inactive ingredients include deionized water, methylpropanediol, phenoxyethanol, cetyl lactate, glycerin, hydroxypropyl cellulose polyquaternium-6, behentrimonium methosulfate, and fragrascent powder.

The Examples were tested under the FDA TFM healthcare personnel hand wash hand scrub test. Here, 8 participants were used for testing. An appropriate volume of the sample to be tested was placed into the palm of one hand and spread evenly over all aspects of the hand and wrist, paying particular attention to the space under the nails, cuticles, and interdigital spaces. The participants were instructed to rub their hands vigorously until dry. The critical performance properties for the test products are: a 2 $\log_{10}$ reduction in the concentration of the marker organism (*Serratia marcescens*) following first wash, and a 3 $\log_{10}$ reduction in the concentration of the marker organism (*Serratia marcescens*) following 10th wash.

The antimicrobial efficacy test data for Examples 1-4 is presented in Table 3. It can be seen that, for Example 1, the efficacy declines with multiple wash cycles, whereas for Example 2, the efficacy increases.

TABLE 3

| EXAMPLE | MEAN $\log_{10}$ REDUCTION WASH 1 | MEAN $\log_{10}$ REDUCTION WASH 10 |
| --- | --- | --- |
| 1 | 4.26 | 3.56 |
| 2 | 4.29 | 4.75 |
| 3 | 4.46 | 4.92 |
| 4 | 4.44 | 4.97 |

Examples 5-7 were hydroalcoholic gel formulations. Example 5 contained 70 wt. % ethanol, and conventional amounts of acrylates, crosspolymer, aminomethyl propanol, and white unispheres. The composition of Example 6 was identical to Example 5, except that Example 6 included 0.5 wt. % 1,2-octanediol. The composition of Example 7 was identical to Example 5, except that Example 7 included 1 wt. % decylene glycol.

Examples 5-7 were tested as above for Examples 1-4.

TABLE 4

| EXAMPLE | $\log_{10}$ REDUCTION WASH 1 | $\log_{10}$ REDUCTION WASH 10 |
| --- | --- | --- |
| 5 | 3.69 | 3.29 |
| 6 | 3.97 | 4.30 |
| 7 | 4.30 | 4.11 |

Examples 8-14 contained 35 wt. % ethanol in water. Examples 9-14 additionally contained 2 wt. % of a 1,2-alkane diol, as summarized in the Table below. In vitro efficacy of these compositions was measured against a mixture of *E. coli, S. aureus, E. faecium*, and *S. marcescens* (Group 1). Efficacy was also measured against a mixture of *S. aureus* (MRSA), *P. mirabilis, K. pneumoniae*, and *S. epidermidis* (Group 2). The test was conducted according to the ASTM E 2315 method, "Standard Guide for Assessment of Antimicrobial Activity Using a Time-Kill Procedure." Contact time was 15 seconds. Results are summarized in the table below. It can be seen that alkane diols above a 5 chain carbon length potentiate the rapid antimicrobial activity of alcohol whereas alkane diols below 5 chain carbon length do not.

TABLE 5

| EXAMPLE | 1,2-alkane diol | $\log_{10}$ REDUCTION GROUP 1 | $\log_{10}$ REDUCTION GROUP 2 |
|---|---|---|---|
| 8 | — | 0.65 | 0.76 |
| 9 | 1,2-propane diol | 0.63 | 1.27 |
| 10 | 1,2-butane diol | 0.86 | 0.70 |
| 11 | 1,2-pentane diol | 0.82 | 1.31 |
| 12 | 1,2-hexane diol | 3.06 | 1.76 |
| 13 | 1,2-octane diol | >6.16 | >6.21 |
| 14 | 1,2-decane diol | >6.28 | >6.34 |

Examples 15-18 contained a wipe composition and a wipe substrate. The wipe compositions are as shown in the table below. Examples 15-18 were tested as described above for Examples 5-7. Results are reported in the table below. Surprisingly, it can be seen that only those compositions containing a 1,2-alkane diol have increased efficacy at wash 10.

TABLE 6

| EXAMPLE | COMPOSITION | $\log_{10}$ REDUCTION WASH 1 | $\log_{10}$ REDUCTION WASH 10 |
|---|---|---|---|
| 15 | 70 wt. % ethanol on SMS substrate, untreated | 3.05 | 2.09 |
| 16 | 70 wt. % ethanol + 0.5 wt. % 1,2-octanediol on SMS substrate, untreated | 3.86 | 4.44 |
| 17 | 80 wt. % ethanol on SMS substrate, untreated | 3.37 | 2.03 |
| 18 | 0.1 wt. % benzalkonium chloride in water on SMS substrate, untreated | 2.22 | 0.91 |

Examples 19-22 contain varying amounts of 1,2-octanediol in water, as summarized in the table below. In vitro efficacy of these compositions was measured against *E. coli, S. aureus, E. faecium, S. marcescens, S. aureus* (MRSA), *P. mirabilis, K. pneumoniae*, and *S. epidermidis*. The test was conducted according to the ASTM E 2315 method, "Standard Guide for Assessment of Antimicrobial Activity Using a Time-Kill Procedure." Contact time was 15 seconds. Results are summarized in the table below.

TABLE 7

| EXAMPLE | WT. % DIOL (IN WATER) | E. coli 11229 | S. Marcenscens 14756 | Klebsiella pneumoniae 13883 | S. aureus 6538 | Candida tropicals 13803 | Candida albicans 14053 | S. aureus (MRSA) 33591 | S. epidermis 12228 |
|---|---|---|---|---|---|---|---|---|---|
| 19 | 1 | 3.6 | >5.3 | nt | 0.8 | 2.3 | 0.6 | 0.7 | 0.5 |
| 20 | 0.5 | 0.0 | 0.2 | 0.0 | 0.0 | 0.0 | 0.0 | −0.2 | 0.1 |
| 21 | 0.25 | −0.2 | 0.2 | −0.1 | 0.1 | 0.0 | 0.0 | −0.2 | −0.1 |
| 22 | 0.125 | 0.0 | 0.0 | 0.1 | 0.0 | nt | nt | nt | nt |

Examples 23-25 contain varying amounts of ethanol and 1,2-octanediol, as summarized in the tables below. In vitro efficacy of these compositions was measured against *S. marcescen*, and *S. aureus*. The test was conducted according to the ASTM E 2315 method, "Standard Guide for Assessment of Antimicrobial Activity Using a Time-Kill Procedure." Contact time was 15 seconds. Results are summarized in the tables below.

TABLE 8

Log Reduction - *S. marcescens* #14756

| Wt. % DIOL | Wt. % ETHANOL | | |
|---|---|---|---|
| | 0 | 15 | 30 |
| 1.0 | 3.5 | 2.3 | >5.1 |
| 0.5 | 0.3 | 0.1 | >5.1 |
| 0 | nt | nt | 0.45 |

TABLE 9

Log Reduction - *S. aureus* #6538

| Wt. % DIOL | Wt. % ETHANOL | | |
|---|---|---|---|
| | 0 | 15 | 30 |
| 1.0 | 0.2 | 2.6 | 0.9 |
| 0.5 | 0 | 0.2 | 0.1 |
| 0 | nt | nt | 0 |

Thus, it should be evident that the invention herein is advantageous for several reasons including that additional antimicrobial compounds are not needed in the formulations to pass the required healthcare personnel hand wash scrub test. This is advantageous because additional antimicrobial agents can be irritating or even sensitizing to the skin, they add undue cost and manufacturing time to the formulations, and many have regulatory limitations preventing commercial sale worldwide. In one or more embodiments, the antimicrobial composition of the present invention provides a 3 log reduction or greater against gram positive and gram negative bacteria each time the product is used as directed.

Advantageously, the rapid efficacy of the compositions of the present invention provides adequate log reduction when less product is used than with conventional compositions. When less product can be used, a shorter amount of time is required for the product to be applied to the skin and dried. Thus, the time required for effective hand wash is reduced.

Furthermore, in one or more embodiments, the compositions of the present invention provide sustained or persistent protection. The compositions exhibit moisturizing properties, and dispenser clogging and mis-directed output is reduced.

In one or more embodiments, the antimicrobial composition of this invention provides good product stability over a long-term shelf life. In certain embodiments, the stability of the antimicrobial compositions of the present invention is better than the stability of products that are emulsions or solid suspensions. Product stability includes physical properties such as stable viscosity and pH readings over time. Also, product stability requires that the products retain a uniform consistency and appearance, and color and odor must not significantly change so that aged product is different from freshly manufactured product. In one or more embodiments, the antimicrobial compositions of the present invention exhibit good product stability over a shelf-life of about three years.

Various modifications and alterations that do not depart from the scope and spirit of this invention will become apparent to those skilled in the art. This invention is not to be duly limited to the illustrative embodiments set forth herein.

What is claimed is:

1. A method for skin sanitization, the method comprising: contacting the skin with foam formed from a foamable antimicrobial composition comprising at least 50 wt. % of a $C_{1-6}$ alcohol, from about 0.02 to about 10 wt. % of a $C_{6-10}$ alkane diol, based upon the total weight of the antimicrobial composition; and a foaming surfactant selected from the group consisting of siloxane polymer surfactants and fluorosurfactants, wherein the antimicrobial composition is devoid of auxiliary antimicrobial agents.

2. The method of claim 1, wherein the diol is 1,2-hexanediol, 1,2-octanediol, 1,9-nonanediol, 1,2-decanediol, 1,10-decanediol, or a mixture thereof.

3. The method of claim 1, wherein the diol is a $C_{6-8}$ alkane diol, or mixture thereof.

4. The method of claim 1, wherein the diol is present in an amount of at least 0.05 wt. %, based upon the total weight of the antimicrobial composition.

5. The method of claim 1, wherein the diol is present in an amount of from about 0.2 to about 0.75 wt. %, based upon the total weight of the antimicrobial composition.

6. The method of claim 1, wherein the foamable composition comprises from about 0.002 to about 4 wt. % of a siloxane polymer surfactant, based upon the total weight of the foamable composition.

7. The method of claim 1, wherein the foaming surfactant comprises a siloxane polymer surfactant that may be represented by the formula

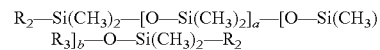

where $R_2$ and $R_3$ independently include a methyl group or a moiety that may be represented by the formula

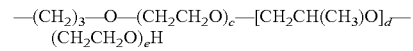

with the proviso that both $R_2$ and $R_3$ are not $CH_3$, where a is an integer from about 3 to about 21, b is an integer from about 1 to about 7, c is an integer from about 0 to about 40, d is an integer from about 0 to about 40, and e is an integer from about 0 to about 40, with the proviso that $a>3\times b$ and that $c+d+e>5$.

8. The method of claim 1, wherein the antimicrobial composition comprises at least 60 wt. % alcohol, based upon the total weight of the antimicrobial composition.

9. The method of claim 1, wherein the alcohol is methanol, ethanol, propanol, butanol, pentanol, hexanol, or mixtures thereof.

10. A method for surface sanitization, the method comprising:
contacting the surface with foam formed from a foamable antimicrobial composition comprising at least 50 wt. % of a $C_{1-6}$ alcohol, from about 0.02 to about 10 wt. % of 1,2-octane diol, and from about 0.002 to about 4 wt. % of a siloxane polymer surfactant, based upon the total weight of the antimicrobial composition, wherein the composition is devoid of auxiliary antimicrobial agents.

11. The method of claim 1, wherein the tested antimicrobial composition provides a $\log_{10}$ reduction of at least 2 after one wash, and at least 3 after ten washes.

12. The method of claim 1, wherein the tested antimicrobial composition provides a $\log_{10}$ reduction of at least 3 after one wash, and at least 4 after ten washes.

* * * * *